United States Patent
Tsujimoto (10) Patent No.: US 11,299,775 B2
(45) Date of Patent: Apr. 12, 2022

(54) METHOD FOR DESIGNING PRIMER, PRIMER, PRIMER SET, DNA AMPLIFICATION METHOD, AND ANALYSIS METHOD

(71) Applicant: FUJIFILM Corporation, Tokyo (JP)

(72) Inventor: Takayuki Tsujimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1065 days.

(21) Appl. No.: 15/921,061

(22) Filed: Mar. 14, 2018

(65) Prior Publication Data

US 2018/0201988 A1    Jul. 19, 2018

Related U.S. Application Data

(63) Continuation of application No. PCT/JP2016/076732, filed on Sep. 12, 2016.

(30) Foreign Application Priority Data

Sep. 30, 2015 (JP) .............................. JP2015-194734

(51) Int. Cl.
| | | |
|---|---|---|
| C12Q 1/6853 | (2018.01) | |
| G16B 25/00 | (2019.01) | |
| C12N 15/09 | (2006.01) | |
| C12Q 1/68 | (2018.01) | |
| G16B 25/20 | (2019.01) | |

(52) U.S. Cl.
CPC ........... *C12Q 1/6853* (2013.01); *C12N 15/09* (2013.01); *C12Q 1/68* (2013.01); *G16B 25/00* (2019.02); *G16B 25/20* (2019.02)

(58) Field of Classification Search
CPC ........ C12Q 1/6853; C12Q 1/68; G16B 25/00; C12N 15/09
USPC .......................................................... 703/11
See application file for complete search history.

(56) References Cited

U.S. PATENT DOCUMENTS

| | | |
|---|---|---|
| 2006/0263789 A1 | 11/2006 | Kincaid |
| 2009/0061440 A1 | 3/2009 | Tanabe et al. |
| 2010/0070452 A1 | 3/2010 | Nakamura |
| 2013/0137587 A1 | 5/2013 | Van Eijk et al. |
| 2015/0203905 A1 | 7/2015 | Takahashi et al. |

FOREIGN PATENT DOCUMENTS

| | | |
|---|---|---|
| JP | 2013-528058 A | 7/2013 |
| WO | 2007/055255 A1 | 5/2007 |
| WO | 2008/004691 A1 | 1/2008 |
| WO | 2012/142213 A2 | 10/2012 |
| WO | 2013/162026 A1 | 10/2013 |

OTHER PUBLICATIONS

Christian Gabriel et al., "Rapid high-throughput human leukocyte antigen typing by massively parallel pyrosequesncing for high-resolution allele identification", Human Immunology, 2009, vol. 70, pp. 960-964. (Nov. 1, 2009).
Diana Rigola et al., "High-Throughput Detection of Induced Mutations and Natural Variation Using KeyPoint™ Technology", PLoS One, Mar. 1, 2009, vol. 4, Issue 3, e4761, pp. 1-9.
Communication dated Jun. 5, 2018 from the European Patent Office in counterpart Application No. 16851105.3.
International Search Report dated Dec. 6, 2016, issued by the International Searching Authority in application No. PCT/JP2016/076732.
Written Opinion dated Dec. 6, 2016, issued by the International Searching Authority in application No. PCT/JP2016/076732.
International Preliminary on Patentability Report dated Apr. 3, 2018, issued by the International Searching Authority in application No. PCT/JP2016/076732.
Communication dated Aug. 7, 2018 issued by the Japanese Patent Office in counterpart application No. 2015-194734.
Communication dated Feb. 26, 2019, from the Japanese Patent Office in counterpart application No. 2015-194734.
Beare, et al., "Candidate Antigens for Q Fever Serodiagnosis Revealed by Immunoscreening of a *Coxiella burnetii* Protein Microarray", Clinical and Vaccine Immunology, vol. 15, No. 12, Dec. 2008, pp. 1771-1779 (10 pages total).

*Primary Examiner* — Jerry Lin
(74) *Attorney, Agent, or Firm* — Sughrue Mion, PLLC (57) ABSTRACT

A method for designing a primer supplied to a PCR reaction includes a primer designing step of defining a 5'-end-side base sequence of the primer so as to include a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product.

11 Claims, 6 Drawing Sheets

FIG. 1A  FIRST CYCLE

FIG. 1B  SECOND CYCLE

FIG. 1C THIRD CYCLE

FIG. 1D FOURTH CYCLE

FIG. 2C (THIRD CYCLE)

FIG. 2D (FOURTH CYCLE)

FIG. 3A  FIRST CYCLE

FIG. 3B  SECOND CYCLE

FIG. 3C (THIRD CYCLE)

FIG. 3D (FOURTH CYCLE)

METHOD FOR DESIGNING PRIMER, PRIMER, PRIMER SET, DNA AMPLIFICATION METHOD, AND ANALYSIS METHOD

CROSS-REFERENCE TO RELATED APPLICATIONS

This application is a Continuation of PCT International Application No. PCT/JP2016/076732, filed on Sep. 12, 2016, which claims priority under 35 U.S.C. § 119(a) to Japanese Patent Application No. 2015-194734, filed on Sep. 30, 2015. Each of the above application(s) is hereby expressly incorporated by reference, in its entirety, into the present application.

BACKGROUND OF THE INVENTION

1. Field of the Invention

The present invention relates to a method for designing a primer, a primer, a primer set, a DNA amplification method, and an analysis method.

2. Description of the Related Art

DNA sequencers and the like, which have been progressing in recent years, facilitate gene analysis. However, in general, a genome has a very large total base length, while sequencers have limited reading capabilities. Thus, a technique of amplifying only a necessary specific gene region and reading only its base sequence to thereby perform efficient and accurate gene analysis, namely, a PCR method is commonly used. In particular, a technique of simultaneously supplying plural primer species to a single PCR reaction system to thereby selectively amplify plural gene regions is referred to as multiplex PCR.

However, in general, multiplex PCR exhibits different amplification capabilities among regions, which adversely affects analysis, such as determination of chromosome count. In the case of diploid organisms such as humans, different amplification capabilities are exhibited among alleles, which adversely affects identification of genotype of SNP. In particular, this is noticeable in a case where the amount of target DNA is small, such as single-cell analysis.

WO2008/004691A describes the following: in order to perform stable multiplex PCR without interference between primers, primers are subjected to local alignment to avoid use of primer sets that cause annealing between primers and formation of dimers, and, instead, primers having sufficiently low complementarity are used to perform efficient multiplex PCR.

SUMMARY OF THE INVENTION

However, even when primers are carefully designed with local alignment of primers such that primers have sufficiently low complementarity to each other, PCR amplification efficiency varies among regions and among alleles, which adversely affects determination of chromosome amount or identification of genotype. In particular, this is noticeable in a case where the target is a small amount of DNA, such as single-cell analysis.

Accordingly, an object of the present invention is to provide a method for designing a primer, the method enabling designing of a primer that enables correction of DNA-amplification variations in regions or DNA-amplification variations in alleles due to a PCR reaction, to thereby enable accurate determination of chromosome amount or accurate identification of genotype.

The inventor of the present invention performed thorough studies on how to achieve the object. As a result, the inventor has found the following: a primer is designed by a method for designing a primer supplied to a PCR reaction, the method including a primer designing step of defining a 5'-end-side base sequence of the primer so as to include a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product; this primer enables correction of DNA-amplification variations in regions or DNA-amplification variations in alleles due to the PCR reaction to thereby perform accurate determination of chromosome amount or accurate identification of genotype. Thus, the inventor has accomplished the present invention.

Specifically, the present invention provides the following [1] to [9].

[1] A method for designing a primer supplied to a PCR reaction, the method including:

a primer designing step of defining a 5'-end-side base sequence of the primer so as to include a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product.

[2] The method for designing a primer supplied to a PCR reaction according to [1] above, wherein, in the primer designing step, the primer is a primer used in N-th and N+1-th thermal cycles, N represents an odd number of 1 or more, when N=1, the step includes defining a complementary DNA fragment constituted by a base sequence that complementarily binds to a 3' end side of an amplification target region in amplification target DNA; defining a non-complementary DNA fragment constituted by a base sequence that does not complementarily bind to the amplification target region; and coupling the non-complementary DNA fragment to a 5' end of the complementary DNA fragment; and when N≥3, the step includes defining a complementary DNA fragment constituted by a base sequence of a non-complementary DNA fragment of a primer used in an N−2-th thermal cycle; defining a non-complementary DNA fragment constituted by a base sequence that is different from each one of base sequences of non-complementary DNA fragments of primers used in 1st to N−2-th thermal cycles, and that does not complementarily bind to the amplification target region; and coupling the non-complementary DNA fragment to a 5' end of the complementary DNA fragment.

[3] The method for designing a primer supplied to a PCR reaction according to [1] above, wherein, in the primer designing step, the primer is a primer used in an N-th thermal cycle, N represents an integer of 1 or more, when N=1, the step includes defining a complementary DNA fragment constituted by a base sequence that complementarily binds to a 3' end side of an amplification target region in amplification target DNA; defining a non-complementary DNA fragment constituted by a base sequence that does not complementarily bind to the amplification target region; and coupling the non-complementary DNA fragment to a 5' end of the complementary DNA fragment;

when N=2, the step includes defining a complementary DNA fragment constituted by a base sequence that complementarily binds to a 3' end side of an amplification target region in amplification target DNA; defining a non-complementary DNA fragment constituted by a base sequence that is different from the base sequence of the non-complementary DNA fragment of the primer used in the 1st thermal cycle, and that does not complementarily bind to the amplification target region; and coupling the non-complementary DNA fragment to a 5' end of the complementary DNA fragment; and when N≥3, the step includes defining a complementary DNA fragment constituted by a base sequence of a non-complementary DNA fragment of a primer used in an N−2-th thermal cycle; defining a non-complementary DNA fragment constituted by a base sequence that is different from each one of base sequences of non-complementary DNA fragments of primers used in 1st to N−1-th thermal cycles, and that does not complementarily bind to the amplification target region; and coupling the non-complementary DNA fragment to a 5' end of the complementary DNA fragment.

[4] A primer designed by the method for designing a primer according to any one of [1] to [3] above.
[5] A primer set supplied to a PCR reaction, the primer set including the primer according to [4] above.
[6] A primer set supplied to a PCR reaction, the primer set including a plurality of the primer sets according to [5] above.
[7] A DNA amplification method including supplying the primer set according to [5] or [6] above to a PCR reaction.
[8] A method for analyzing base-sequence data of an amplification product obtained by supplying the primer set according to [5] or [6] above to a PCR reaction to amplify a plurality of regions, the method including:
performing correction for each of coverages of the regions in accordance with numbers of successful PCR times in the amplification product.
[9] A method for analyzing base-sequence data of an amplification product obtained by supplying the primer set according to [5] or [6] above to a PCR reaction to amplify a region including at least one locus, the method including:
performing correction for each of coverages of alleles in accordance with numbers of successful PCR times in the amplification product.

The present invention provides a method for designing a primer, the method enabling designing of a primer that enables correction of DNA-amplification variations in regions or DNA-amplification variations in alleles due to a PCR reaction, to thereby enable accurate determination of chromosome amount or accurate identification of genotype.

DESCRIPTION OF THE PREFERRED EMBODIMENTS

<PCR> PCR (polymerase chain reaction) is an approach, a technique, or a reaction for amplifying DNA (deoxyribonucleic acid). The technique may be referred to as a PCR method, and the reaction may be referred to as a PCR reaction. In the PCR reaction, thermal cycles are not necessarily performed continuously: for example, at the start time, an intermediate time, or the finish time of each thermal cycle, a substance may be added to or removed from the reaction solution.

<SNP> SNP (single nucleotide polymorphism) is variation in a population due to a variation of a single base in the base sequence of the genome where the frequency of the variation in the population is 1% or more.

Method for Designing Primer

A method for designing a primer according to the present invention includes a primer designing step of defining a 5'-end-side base sequence of the primer so as to include a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product.

In general, in a PCR reaction, a thermal cycle including the following three steps is repeated plural times to thereby amplify an amplification target region of amplification target DNA: a denaturation step of separating double-stranded DNA into single-stranded DNA, an annealing step of binding primers to the single-stranded DNA, and an extension step of synthesizing DNA complementary to the single-stranded DNA from the 3' ends of the primers as starting points. Thus, when an identification tag sequence is incorporated onto the 5' end of such a primer, the tag sequence enabling identification of the primer, DNA molecules in an amplification product generated in a PCR reaction performed with the primer have, in their base sequences, a base sequence that is the same as or complementary to the identification tag sequence. In other words, this tag sequence is a base sequence or its complementary base sequence, the base sequence enabling identification of, among thermal cycles in the PCR reaction, the synthesis cycle of a DNA molecule in the amplification product obtained by the PCR reaction performed with the primer, the identification being based on base-sequence data obtained by sequencing the amplification product.

The base sequence or its complementary base sequence, the base sequence enabling identification of the synthesis cycle, will be described more specifically in the description of a DNA amplification method according to the present invention.

In a method for designing a primer according to the present invention, primers can be designed such that the primers are not annealed with each other to form dimers. For example, on the basis of the disclosure of WO2008/004691A, primers can be designed, by subjecting primers to local alignment with each other, so as to avoid combinations of primers that are annealed with each other to form dimers.

The primer designing step may include defining a complementary DNA fragment constituted by a base sequence that complementarily binds to an amplification target region in amplification target DNA, defining a non-complementary DNA fragment constituted by a base sequence that does not complementarily bind to the amplification target region, and coupling the non-complementary DNA fragment to the 5' end of the complementary DNA fragment. The base sequence of the non-complementary DNA fragment is constituted by a base sequence or its complementary base sequence, the base sequence enabling identification of the synthesis cycle.

In the primer designing step, in a case where the primer is a primer used in N-th and N+1-th thermal cycles and N represents an odd number of 1 or more, when N=1, the step preferably includes defining a complementary DNA fragment constituted by a base sequence that complementarily binds to a 3' end side of an amplification target region in amplification target DNA; defining a non-complementary DNA fragment constituted by a base sequence that does not complementarily bind to the amplification target region; and coupling the non-complementary DNA fragment to a 5' end of the complementary DNA fragment; and, when N≥3, the step preferably includes defining a complementary DNA fragment constituted by a base sequence of a non-complementary DNA fragment of a primer used in an N−2-th thermal cycle; defining a non-complementary DNA fragment constituted by a base sequence that is different from each one of base sequences of non-complementary DNA fragments of primers used in 1st to N−2-th thermal cycles, and that does not complementarily bind to the amplification target region; and coupling the non-complementary DNA fragment to a 5' end of the complementary DNA fragment.

This method for designing a primer provides an advantage of a reduction in the number of primers designed, compared with the case of designing a primer for each of thermal cycles (N represents an odd number of 1 or more).

Alternatively, in the primer designing step, in a case where the primer is a primer used in an N-th thermal cycle and N represents an integer of 1 or more, when N=1, the step preferably includes defining a complementary DNA fragment constituted by a base sequence that complementarily binds to a 3' end side of an amplification target region in amplification target DNA; defining a non-complementary DNA fragment constituted by a base sequence that does not complementarily bind to the amplification target region; and coupling the non-complementary DNA fragment to a 5' end of the complementary DNA fragment; when N=2, the step preferably includes defining a complementary DNA fragment constituted by a base sequence that complementarily binds to a 3' end side of an amplification target region in amplification target DNA; defining a non-complementary DNA fragment constituted by a base sequence that is different from the base sequence of the non-complementary DNA fragment of the primer used in the 1st thermal cycle, and that does not complementarily bind to the amplification target region; and coupling the non-complementary DNA fragment to a 5' end of the complementary DNA fragment; and, when N≥3, the step preferably includes defining a complementary DNA fragment constituted by a base sequence of a non-complementary DNA fragment of a primer used in an N−2-th thermal cycle; defining a non-complementary DNA fragment constituted by a base sequence that is different from each one of base sequences of non-complementary DNA fragments of primers used in 1st to N−1-th thermal cycles, and that does not complementarily bind to the amplification target region; and coupling the non-complementary DNA fragment to a 5' end of the complementary DNA fragment.

This method for designing a primer provides primers whose 5'-end-side base sequences are individually unique to corresponding thermal cycles. This enables easier identification of synthesis cycles of DNA molecules in an amplification product.

Primer and Primer Set

A primer according to the present invention is a primer designed by the above-described method for designing a primer according to the present invention, and supplied to a PCR reaction.

Thus, a primer according to the present invention is a primer supplied to a PCR reaction, and the 5'-end-side base sequence of the primer includes a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product.

A primer according to the present invention may be a primer constituted by a complementary DNA fragment constituted by a base sequence that complementarily binds to an amplification target region in amplification target DNA, and a non-complementary DNA fragment constituted by a base sequence that is coupled to the 5' end of the complementary DNA fragment and that does not complementarily bind to the amplification target region. The base sequence of the non-complementary DNA fragment is constituted by a base sequence or its complementary base sequence, the base sequence enabling identification of, among thermal cycles in the PCR reaction, a synthesis cycle of a DNA molecule in an amplification product obtained by the PCR reaction performed with the primer, the identification being based on base-sequence data obtained by sequencing the amplification product.

In a case where the above-described primer is a primer used in N-th and N+1-th thermal cycles where N represents an odd number of 1 or more, a primer according to the present invention is preferably constituted by, when N=1, a complementary DNA fragment constituted by a base sequence that complementarily binds to the 3' end side of an amplification target region in amplification target DNA, and a non-complementary DNA fragment constituted by a base sequence that is coupled to the 5' end of the complementary DNA fragment, and that does not complementarily bind to the amplification target region; and, when N≥3, the primer is preferably constituted by a complementary DNA fragment constituted by the base sequence of the non-complementary DNA fragment of the primer used in the N−2-th thermal cycle, and a non-complementary DNA fragment constituted by a base sequence that is coupled to the 5' end of the complementary DNA fragment, that is different from the base sequence of the non-complementary DNA fragment of the primer used in the N−2-th thermal cycle, and that does not complementarily bind to the amplification target region.

In a case where the above-described primer is a primer used in an N-th thermal cycle where N represents an integer of 1 or more, a primer according to the present invention is preferably constituted by, when N=1, a complementary DNA fragment constituted by a base sequence that complementarily binds to the 3' end side of an amplification target region in amplification target DNA, and a non-complementary DNA fragment constituted by a base sequence that is coupled to the 5' end of the complementary DNA fragment, and that does not complementarily bind to the amplification target region; when N=2, the primer is preferably constituted by a complementary DNA fragment constituted by a base sequence that complementarily binds to the 3' end side of an amplification target region of amplification target DNA, and a non-complementary DNA fragment constituted by a base sequence that is coupled to the 5' end of the complementary DNA fragment, that is different from the base sequence of the non-complementary DNA fragment of the primer used in the 1st thermal cycle, and that does not complementarily bind to the amplification target region; and, when N≥3, the primer is preferably constituted by a complementary DNA fragment constituted by the base sequence of the non-complementary DNA fragment of the primer used in the N−2-th thermal cycle, and a non-complementary DNA fragment constituted by a base sequence that is coupled to the 5' end of the complementary DNA fragment, that is different from each one of the base sequences of the non-complementary DNA fragments of the primers used in the 1st to N−1-th thermal cycles, and that does not complementarily bind to the amplification target region.

A primer according to the present invention can be produced, in accordance with the oligonucleotide base sequence designed by the above-described method for designing a primer according to the present invention, by a known method for synthesizing an oligonucleotide.

A primer set according to the present invention is a primer set that includes the above-described primer according to the present invention and is supplied to a PCR reaction.

A primer set according to the present invention is preferably a primer set supplied to a PCR reaction, the primer set being constituted by a combination of a first primer selected from the group consisting of the above-described primers according to the present invention, and a second primer; and the pair of the first primer and the second primer is used to amplify an amplification target region of amplification target DNA by a PCR reaction. More preferably, the second primer is selected from the group consisting of the above-described primers according to the present invention.

When both of the first primer and the second primer are primers selected from the group consisting of the above-described primers according to the present invention, the base sequence of such a primer can be added to the 5' end side of a DNA molecule in an amplification product from a PCR reaction, and a base sequence complementary to the base sequence of the primer can be added to the 3' end side of a DNA molecule. This enables more accurate identification of the synthesis cycle of DNA molecules. An identical primer set can be used in an odd-numbered cycle and an even-numbered cycle to achieve a reduction in the number of steps.

When the first primer alone is a primer selected from the group consisting of the above-described primers according to the present invention, an identical primer can be used as the second primer through all cycles of the PCR reaction. This enables a reduction in the number of steps for designing a primer.

Another primer set according to the present invention is a primer set that includes a plurality of the above-described primer sets according to the present invention and is supplied to a PCR reaction.

This primer set is suitably used for multiplex PCR.

DNA Amplification Method

A DNA amplification method according to the present invention is a DNA amplification method including supplying, to a PCR reaction, the above-described primer set according to the present invention.

An amplification product generated by a DNA amplification method according to the present invention is sequenced, which enables identification of, in the PCR reaction, the synthesis cycle of a DNA molecule in the amplification product.

A DNA amplification method according to the present invention broadly includes three embodiments: (1) a method in which both paired primers are primers having non-complementary DNA fragments at the 5' end sides, and an identical primer set is used in an odd-numbered PCR reaction cycle and its subsequent even-numbered PCR reaction cycle (refer to FIGS. 1A to 1D), (2) a method in which both paired primers are primers having non-complementary DNA fragments at the 5' end sides, and a different primer set is used in each PCR reaction cycle (refer to FIGS. 2A to 2D), and (3) a method in which only one of paired primers is a primer having a non-complementary DNA fragment at the 5' end side, and a different primer set is used in each PCR reaction cycle (refer to FIGS. 3A to 3D).

Hereinafter, these three embodiments will be individually described.

(1) Method in which Both Paired Primers are Primers Having Non-Complementary DNA Fragments at 5' End Sides, and Identical Primer Set is Used in Odd-Numbered PCR Reaction Cycle and its Subsequent Even-Numbered PCR Reaction Cycle Hereinafter, the method will be described with some reference to FIGS. 1A to 1D.

In the first cycle of a PCR reaction (refer to FIG. 1A), genome DNA is used as the amplification target DNA (template DNA), and a primer set is applied to this amplification target DNA, the primer set being constituted by a primer $F_1$ (denoted by "PRIMER F1" in FIG. 1A) constituted by a complementary DNA fragment constituted by a base sequence $A_0$ (denoted by "A0" in FIG. 1A) annealed with the amplification target region of the first strand of the amplification target DNA, and a non-complementary DNA fragment constituted by a base sequence $A_1$ (denoted by "A1" in FIG. 1A) that is coupled to the 5' end of the complementary DNA fragment, and that is not annealed with the amplification target region; and a primer $R_1$ (denoted by "PRIMER R1" in FIG. 1A) constituted by a complementary DNA fragment constituted by a base sequence $B_0$ (denoted by "B0" in FIG. 1A) annealed with the amplification target region of the second strand of the amplification target DNA, and a base sequence $B_1$ (denoted by "B1" in FIG. 1A) that is coupled to the 5' end of the complementary DNA fragment and that is not annealed with the amplification target region.

The first cycle of the PCR reaction (refer to FIG. 1A) synthesizes a DNA molecule having, at the 5' end, the base sequence $A_1$ derived from the non-complementary DNA fragment of the primer $F_1$; and a DNA molecule having, at the 5' end, the base sequence $B_1$ derived from the non-complementary DNA fragment of the primer $R_1$.

In the second cycle of the PCR reaction (refer to FIG. 1B), the amplification product generated in the first cycle of the PCR reaction is used as the amplification target DNA, and the same primer set as in the first cycle, the primer set being constituted by the primer $F_1$ and the primer $R_1$, is applied to the amplification target DNA.

The second cycle of the PCR reaction (refer to FIG. 1B) synthesizes a DNA molecule having, at the 5' end, the base sequence $A_1$ derived from the non-complementary DNA fragment of the primer $F_1$, and having, at the 3' end, a base sequence b₁ (denoted by "b1" in FIG. 1B) complementary to the base sequence $B_1$ of the non-complementary DNA fragment of the primer $R_1$; and a DNA molecule having, at the 5' end, the base sequence $B_1$ derived from the non-complementary DNA fragment of the primer $R_1$, and having, at the 3' end, a base sequence $a_1$ (denoted by "a1" in FIG. 1B) complementary to the base sequence $A_1$ of the non-complementary DNA fragment of the primer $F_1$.

In the third cycle of the PCR reaction (refer to FIG. 1C), the amplification product generated in the second cycle of the PCR reaction is used as the amplification target DNA (template DNA), and a primer set is applied to this amplification target DNA, the primer set being constituted by a primer $F_2$ (denoted by "PRIMER F2" in FIG. 1C) constituted by a complementary DNA sequence constituted by a base sequence $A_1$ annealed with the 3' end side of the amplification target region of the first strand of the amplification target DNA, and a non-complementary DNA fragment constituted by a base sequence $A_2$ (denoted by "A2" in FIG. 1C) that is coupled to the 5' end of the complementary DNA fragment, and that is not annealed with the amplification target region; and a primer $R_2$ (denoted by "PRIMER R2" in FIG. 1C) constituted by a complementary DNA sequence constituted by a base sequence $B_1$ annealed with the 3' end side of the amplification target region of the second strand of the amplification target DNA, and a non-complementary DNA fragment constituted by a base sequence $B_2$ (denoted by "B2" in FIG. 1C) that is coupled to the 5' end of the complementary DNA fragment, and that is not annealed with the amplification target region.

The third cycle of the PCR reaction (refer to FIG. 1C) synthesizes a DNA molecule having, at the 5' end, the base sequence $A_2$ derived from the non-complementary DNA fragment of the primer $F_2$; and a DNA molecule having, at the 5' end, the base sequence $B_2$ derived from the non-complementary DNA fragment of the primer $R_2$.

In the fourth cycle of the PCR reaction (refer to FIG. 1D), the amplification product generated in the third cycle of the PCR reaction is used as the amplification target DNA (template DNA), and the same primer set as in the third cycle (FIG. 1C), the primer set being constituted by the primer $F_2$ and the primer $R_2$, is applied to the amplification target DNA.

The fourth cycle of the PCR reaction (refer to FIG. 1D) synthesizes a DNA molecule having, at the 5' end, the base sequence $A_2$ derived from the non-complementary DNA fragment of the primer $F_2$, and having, at the 3' end, a base sequence $b_2$ (denoted by "b2" in FIG. 1D) complementary to the base sequence $B_2$ of the non-complementary DNA fragment of the primer $R_2$; and a DNA molecule having, at the 5' end, the base sequence $B_2$ derived from the non-complementary DNA fragment of the primer $R_2$, and having, at the 3' end, a base sequence $a_2$ (denoted by "a2" in FIG. 1D) complementary to the base sequence $A_2$ of the non-complementary DNA fragment of the primer $F_2$.

In the fifth and subsequent cycles of the PCR reaction, a $2(i+1)+1$-th cycle and a $2(i+1)+2$-th cycle where i represents an integer of 1 or more are also performed with an identical primer set constituted by primers $F_{i+2}$ and $R_{i+2}$.

The primer $F_{i+2}$ is constituted by a complementary DNA fragment constituted by a base sequence $A_{i+1}$, and a non-complementary DNA fragment constituted by a base sequence $A_{i+2}$ that is coupled to the 5' end of the complementary DNA fragment, and that does not complementarily bind to the amplification target region. The base sequence $A_{i+1}$ of the complementary DNA fragment of the primer $F_{i+2}$ is the same as the base sequence $A_{i+1}$ of the non-complementary DNA fragment of the primer $F_{i+1}$. The base sequence $A_{i+2}$ of the non-complementary DNA fragment of the primer $F_{i+2}$ is different from each one of base sequences $A_1$ to $A_{i+1}$ of the non-complementary DNA fragments of the primer $F_i$ to the primer $F_{i+1}$, and is the same as the base sequence $A_{i+2}$ of the complementary DNA fragment of the primer $F_{i+3}$.

The primer $R_{i+2}$ is constituted by a complementary DNA fragment constituted by a base sequence $B_{i+1}$, and a non-complementary DNA fragment constituted by a base sequence $B_{i+2}$ that is coupled to the 5' end of the complementary DNA fragment, and that does not complementarily bind to the amplification target region. The base sequence $B_{i+1}$ of the complementary DNA fragment of the primer $R_{i+2}$ is the same as the base sequence $B_{i+1}$ of the non-complementary DNA fragment of the primer $R_{1+1}$. The base sequence $B_{i+2}$ of the non-complementary DNA fragment of the primer $R_{i+2}$ is different from the base sequence $B_{i+1}$ of the non-complementary DNA fragment of the primer $R_{i+1}$, and is the same as the base sequence $A_{i+2}$ of the complementary DNA fragment of the primer $F_{i+3}$.

The $2(i+1)+1$-th cycle of the PCR reaction synthesizes a DNA molecule having, at the 5' end, the base sequence $A_{i+2}$ derived from the non-complementary DNA fragment of the primer $F_{i+2}$; and a DNA molecule having, at the 5' end, the base sequence $B_{i+2}$ derived from the non-complementary DNA fragment of the primer $R_{i+2}$. The $2(i+1)+2$-th cycle of the PCR reaction synthesizes a DNA molecule having, at the 5' end, the base sequence $A_{i+2}$ derived from the non-complementary DNA fragment of the primer $F_{i+2}$, and having, at the 3' end, a base sequence $b_{i+2}$ complementary to the base sequence $B_{i+2}$ of the non-complementary DNA fragment of the primer $R_{i+2}$; and a DNA molecule having, at the 5' end, the base sequence $B_{i+2}$ derived from the non-complementary DNA fragment of the primer $B_{i+2}$, and having, at the 3' end, a base sequence $a_{i+2}$ complementary to the base sequence $A_{i+2}$ of the non-complementary DNA fragment of the primer $F_{i+2}$.

A DNA molecule synthesized in the $2(i+1)+1$-th cycle of the PCR reaction and a DNA molecule synthesized in the $2(i+1)+2$-th cycle of the PCR reaction are distinguishable from each other because the latter has, at the 3' end, the base sequence $a_{i+2}$ or $b_{i+2}$ complementary to the base sequence $A_{i+2}$ or $B_{i+2}$ of the non-complementary DNA fragment of the primer.

A DNA molecule synthesized in the $2(i+1)$-th cycle of the PCR reaction and a DNA molecule synthesized in the $2(i+1)+1$-th cycle of the PCR reaction are distinguishable from each other because the latter has, at the 5' end, a base sequence derived from the base sequence $A_{i+2}$ or $B_{i+2}$ of the non-complementary DNA fragment of the primer.

As described above, DNA molecules synthesized in the cycles of the PCR reaction each have, at the 5' end or 3' end, a base sequence enabling identification of the synthesis cycle of the DNA molecule.

This enables identification of, among thermal cycles of the PCR reaction, the synthesis cycle of a DNA molecule in the amplification product obtained by the PCR reaction, the identification being based on base-sequence data obtained by sequencing the amplification product.

Thus, the synthesis cycles of the synthesized DNA molecules are individually identified, so that the maximum number of PCR times of the amplification target region can also be determined.

Incidentally, the last cycle of the PCR reaction may be an even-numbered cycle or an odd-numbered cycle.

(2) Method in which Both Paired Primers are Primers Having Non-Complementary DNA Fragments at 5' End Sides, and Different Primer Set is Used in Each PCR Reaction Cycle Hereinafter, the method will be described with some reference to FIGS. 2A to 2D.

In the first cycle of the PCR reaction (refer to FIG. 2A), genome DNA is used as the amplification target DNA (template DNA), and a primer set is applied to the amplification target DNA, the primer set being constituted by a primer $F_1$ (denoted by "PRIMER F1" in FIG. 2A) constituted by a complementary DNA fragment constituted by a base sequence $A_0$ (denoted by "A0" in FIG. 2A) annealed with the amplification target region of the first strand of the amplification target DNA, and a non-complementary DNA fragment constituted by a base sequence $A_1$ (denoted by "A1" in FIG. 2A) that is coupled to the 5' end of the complementary DNA fragment, and that is not annealed with the amplification target region; and a primer $R_1$ (denoted by "PRIMER R1" in FIG. 2A) constituted by a complementary DNA fragment constituted by a base sequence $B_0$ (denoted by "B0" in FIG. 2A) annealed with the amplification target region of the second strand of the amplification target DNA, and a base sequence $B_1$ (denoted by "B1" in FIG. 2A) that is coupled to the 5' end of the complementary DNA fragment, and that is not annealed with the amplification target region.

The first cycle of the PCR reaction (refer to FIG. 2A) synthesizes a DNA molecule having, at the 5' end, the base sequence $A_1$ derived from the non-complementary DNA fragment of the primer $F_1$; and a DNA molecule having, at the 5' end, the base sequence $B_1$ derived from the non-complementary DNA fragment of the primer $R_1$.

In the second cycle of the PCR reaction (refer to FIG. 2B), the amplification product generated in the first cycle of the PCR reaction is used as the amplification target DNA, and a primer set is applied to this amplification target DNA, the primer set being constituted by a primer $F_2$ (denoted by "PRIMER F2" in FIG. 2B) constituted by a complementary DNA fragment constituted by a base sequence $A_0$ annealed with the amplification target region of the first strand of the amplification target DNA, and a non-complementary DNA fragment constituted by a base sequence $A_2$ (denoted by "A2" in FIG. 2B) that is coupled to the 5' end of the complementary DNA fragment, and that is not annealed with the amplification target region; and a primer $R_2$ (denoted by "PRIMER R2" in FIG. 2B) constituted by a complementary DNA fragment constituted by a base sequence $B_0$ annealed with the amplification target region of the second strand of the amplification target DNA, and a base sequence $B_2$ (denoted by "B2" in FIG. 2B) that is coupled to the 5' end of the complementary DNA fragment, and that is not annealed with the amplification target region.

The second cycle of the PCR reaction (refer to FIG. 2B) synthesizes a DNA molecule having, at the 5' end, the base sequence $A_2$ derived from the non-complementary DNA fragment of the primer $F_2$, and having, at the 3' end, a base sequence $b_1$ (denoted by "b1" in FIG. 2B) complementary to the base sequence $B_1$ of the non-complementary DNA fragment of the primer $R_1$; and a DNA molecule having, at the 5' end, the base sequence $B_2$ derived from the non-complementary DNA fragment of the primer $R_2$, and having, at the 3' end, a base sequence $a_1$ (denoted by "a1" in FIG. 2B) complementary to the base sequence $A_1$ of the non-complementary DNA fragment of the primer $F_1$.

In the third cycle of the PCR reaction (refer to FIG. 2C), the amplification product generated in the second cycle of the PCR reaction is used as the amplification target DNA (template DNA), and a primer set is applied to this amplification target DNA, the primer set being constituted by a primer $F_3$ (denoted by "PRIMER F3" in FIG. 2C) constituted by a complementary DNA sequence constituted by a base sequence $A_1$ annealed with the 3' end side of the amplification target region of the first strand of the amplification target DNA, and a non-complementary DNA fragment constituted by a base sequence $A_3$ (denoted by "A3" in FIG. 2C) that is coupled to the 5' end of the complementary DNA fragment, and that is not annealed with the amplification target region; and a primer $R_3$ (denoted by "PRIMER R3" in FIG. 2C) constituted by a complementary DNA sequence constituted by a base sequence $B_1$ annealed with the 3' end side of the amplification target region of the second strand of the amplification target DNA, and a non-complementary DNA fragment constituted by a base sequence $B_3$ (denoted by "B3" in FIG. 2C) that is coupled to the 5' end of the complementary DNA fragment, and that is not annealed with the amplification target region.

The third cycle of the PCR reaction (refer to FIG. 2C) synthesizes a DNA molecule having, at the 5' end, the base sequence $A_3$ derived from the non-complementary DNA fragment of the primer $F_3$, and having, at the 3' end, a base sequence $b_2$ (denoted by "b2" in FIG. 2C) complementary to the base sequence $B_2$ of the non-complementary DNA fragment of the primer $R_2$ used in the second cycle; and a DNA molecule having, at the 5' end, the base sequence $B_3$ derived from the non-complementary DNA fragment of the primer $R_3$, and having, at the 3' end, a base sequence $a_2$ (denoted by "a2" in FIG. 2C) complementary to the base sequence $A_2$ of the non-complementary DNA fragment of the primer $F_2$ used in the second cycle.

In the fourth cycle of the PCR reaction (refer to FIG. 2D), the amplification product generated in the third cycle of the PCR reaction is used as the amplification target DNA (template DNA), and a primer set is applied to this amplification target DNA, the primer set being constituted by a primer $F_4$ (denoted by "PRIMER F4" in FIG. 2D) constituted by a complementary DNA sequence constituted by a base sequence $A_2$ annealed with the 3' end side of the amplification target region of the first strand of the amplification target DNA, and a non-complementary DNA fragment constituted by a base sequence $A_4$ (denoted by "A4" in FIG. 2D) that is coupled to the 5' end of the complementary DNA fragment, and that is not annealed with the amplification target region; and a primer $R_4$ (denoted by "PRIMER R4" in FIG. 2D) constituted by a complementary DNA sequence constituted by a base sequence $B_2$ annealed with the 3' end side of the amplification target region of the second strand of the amplification target DNA, and a non-complementary DNA fragment constituted by a base sequence $B_4$ (denoted by "B4" in FIG. 2D) that is coupled to the 5' end of the complementary DNA fragment, and that is not annealed with the amplification target region.

The fourth cycle of the PCR reaction (refer to FIG. 2D) synthesizes a DNA molecule having, at the 5' end, the base sequence $A_4$ derived from the non-complementary DNA fragment of the primer $F_4$, and having, at the 3' end, a base sequence $b_3$ (denoted by "b3" in FIG. 2D) complementary to the base sequence $B_3$ of the non-complementary DNA fragment of the primer $R_3$; and a DNA molecule having, at the 5' end, the base sequence $B_4$ derived from the non-complementary DNA fragment of the primer $R_4$, and having, at the 3' end, a base sequence $a_3$ (denoted by "a3" in FIG. 2D) complementary to the base sequence $A_3$ of the non-complementary DNA fragment of the primer $F_3$.

In the fifth and subsequent cycles of the PCR reaction, a j+4-th cycle where j represents an integer of 1 or more is also performed with a primer set constituted by primers $F_{j+4}$ and $R_{j+4}$.

The primer $F_{j+4}$ is constituted by a complementary DNA fragment constituted by a base sequence $A_{j+2}$, and a non-complementary DNA fragment constituted by a base sequence $A_{j+4}$ that is coupled to the 5' end of the complementary DNA fragment, and that does not complementarily bind to the amplification target region. The base sequence $A_{j+2}$ of the complementary DNA fragment of the primer $F_{j+4}$ is the same as the base sequence $A_{j+2}$ of the non-complementary DNA fragment of the primer $F_{j+2}$. The base sequence $A_{j+4}$ of the non-complementary DNA fragment of the primer $F_{j+4}$ is different from each one of the base sequences $A_1$ to $A_{j+3}$ of the non-complementary DNA fragments of the primer $F_1$ to the primer $F_{j+3}$, and is the same as the base sequence $A_{j+4}$ of the complementary DNA fragment of the primer $F_{j+6}$.

The primer $R_{j+4}$ is constituted by a complementary DNA fragment constituted by a base sequence $B_{j+2}$, and a non-complementary DNA fragment constituted by a base sequence $B_{j+4}$ that is coupled to the 5' end of the complementary DNA fragment, and that does not complementarily bind to the amplification target region. The base sequence $B_{j+2}$ of the complementary DNA fragment of the primer $R_{j+4}$ is the same as the base sequence $B_{j+2}$ of the non-complementary DNA fragment of the primer $R_{j+2}$. The base sequence $B_{j+4}$ of the non-complementary DNA fragment of the primer $R_{j+4}$ is different from each one of the base sequences $B_1$ to $B_{j+3}$ of the non-complementary DNA fragments of the primer $R_1$ to the primer $R_{j+3}$, and is the same as the base sequence $B_{j+4}$ of the complementary DNA fragment of the primer $R_{j+6}$.

The j+4-th cycle of the PCR reaction synthesizes a DNA molecule having, at the 5' end, the base sequence $A_{j+4}$ derived from the non-complementary DNA fragment of the primer $F_{j+4}$, and having, at the 3' end, a base sequence $B_{j+3}$ complementary to the base sequence $B_{j+3}$ of the non-complementary DNA fragment of the primer $R_{j+3}$; and a DNA molecule having, at the 5' end, the base sequence $B_{j+4}$ derived from the non-complementary DNA fragment of the primer $R_{j+4}$, and having, at the 3' end, a base sequence $a_{j+3}$ complementary to the base sequence $A_{j+3}$ of the non-complementary DNA fragment of the primer $F_{j+3}$.

As described above, DNA molecules synthesized in the cycles of the PCR reaction each have, at the 5' end, a base sequence enabling identification of the synthesis cycle of the DNA molecule.

This enables identification of, among thermal cycles of the PCR reaction, the synthesis cycle of a DNA molecule in the amplification product obtained by the PCR reaction, the identification being based on base-sequence data obtained by sequencing the amplification product.

Thus, the synthesis cycles of the synthesized DNA molecules are individually identified, so that the maximum number of PCR times of the amplification target region can also be determined.

(3) Method in which Only One of Paired Primers is Primer Having Non-Complementary DNA Fragment at 5' End Side, and Different Primer Set is Used in Each PCR Reaction Cycle Hereinafter, the method will be described with some reference to FIGS. 3A to 3D.

In the first cycle of the PCR reaction (refer to FIG. 3A), genome DNA is used as the amplification target DNA (template DNA), and a primer set is applied to the amplification target DNA, the primer set being constituted by a primer $F_1$ (denoted by "PRIMER F1" in FIG. 3A) constituted by a complementary DNA fragment constituted by a base sequence $A_0$ (denoted by "A0" in FIG. 3A) annealed with the amplification target region of the first strand of the amplification target DNA, and a non-complementary DNA fragment constituted by a base sequence $A_1$ (denoted by "A1" in FIG. 3A) that is coupled to the 5' end of the complementary DNA fragment, and that is not annealed with the amplification target region; and a primer $R_0$ (denoted by "PRIMER R0" in FIG. 3A) constituted by a complementary DNA fragment constituted by a base sequence $B_0$ (denoted by "B0" in FIG. 3A) annealed with the amplification target region of the second strand of the amplification target DNA.

The first cycle of the PCR reaction (refer to FIG. 3A) synthesizes a DNA molecule having, at the 5' end, the base sequence $A_1$ derived from the non-complementary DNA fragment of the primer $F_1$; and a DNA molecule having, at the 5' end, the base sequence $B_0$ derived from the complementary DNA fragment of the primer $R_0$.

In the second cycle of the PCR reaction (refer to FIG. 3B), the amplification product generated in the first cycle of the PCR reaction is used as the amplification target DNA, and a primer set is applied to this amplification target DNA, the primer set being constituted by a primer $F_2$ (denoted by "PRIMER F2" in FIG. 3B) constituted by a complementary DNA fragment constituted by a base sequence $A_0$ annealed with the amplification target region of the first strand of the amplification target DNA, and a non-complementary DNA fragment constituted by a base sequence $A_2$ (denoted by "A2" in FIG. 3B) that is coupled to the 5' end of the complementary DNA fragment, and that is not annealed with the amplification target region; and a primer $R_0$ constituted by a complementary DNA fragment constituted by a base sequence $B_0$ annealed with the amplification target region of the second strand of the amplification target DNA.

The second cycle of the PCR reaction (refer to FIG. 3B) synthesizes a DNA molecule having, at the 5' end, the base sequence $A_2$ derived from the non-complementary DNA fragment of the primer $F_2$; and a DNA molecule having, at the 3' end, a base sequence $a_1$ (denoted by "a1" in FIG. 3B) complementary to the base sequence $A_1$ of the non-complementary DNA fragment of the primer $F_1$.

In the third cycle of the PCR reaction (refer to FIG. 3C), the amplification product generated in the second cycle of the PCR reaction is used as the amplification target DNA (template DNA), and a primer set is applied to this amplification target DNA, the primer set being constituted by a primer $F_3$ (denoted by "PRIMER F3" in FIG. 3C) constituted by a complementary DNA sequence constituted by a base sequence $A_1$ annealed with the 3' end side of the amplification target region of the first strand of the amplification target DNA, and a non-complementary DNA fragment constituted by a base sequence $A_3$ (denoted by "A3" in FIG. 3C) that is coupled to the 5' end of the complementary DNA fragment, and that is not annealed with the amplification target region; and a primer $R_0$ constituted by a complementary DNA sequence constituted by a base sequence $B_0$ annealed with the 3' end side of the amplification target region of the second strand of the amplification target DNA.

Figure 1A:
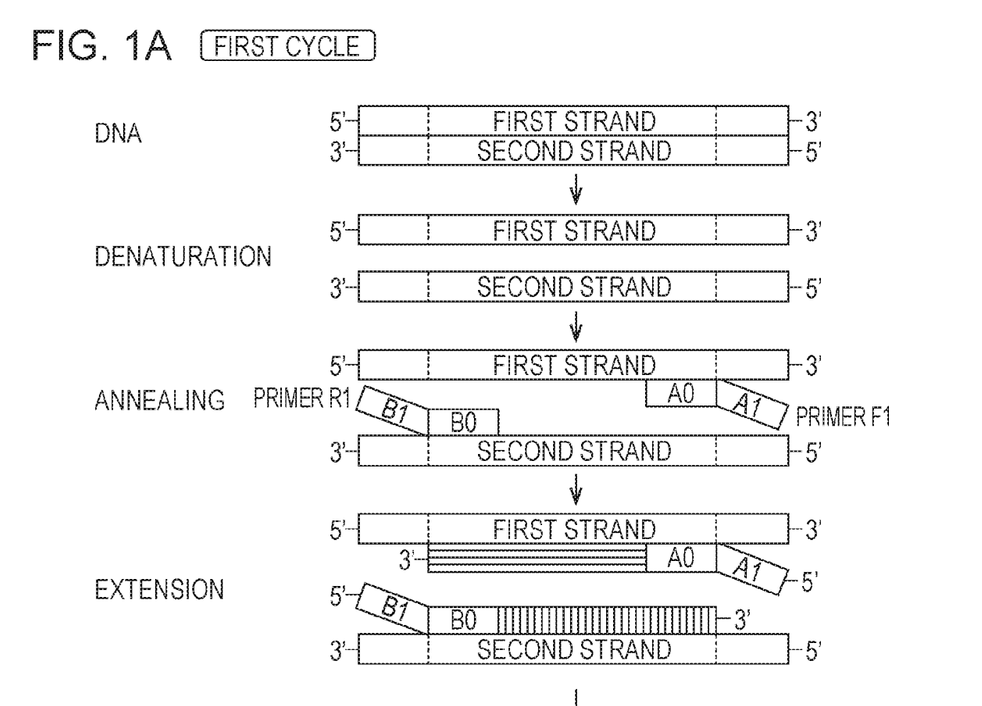
FIGS. 1A to 1D schematically illustrate a DNA amplification method in which both paired primers are primers according to the present invention, and an identical primer set is used in an odd-numbered PCR reaction cycle and its subsequent even-numbered PCR reaction cycle.
Figure 1B:
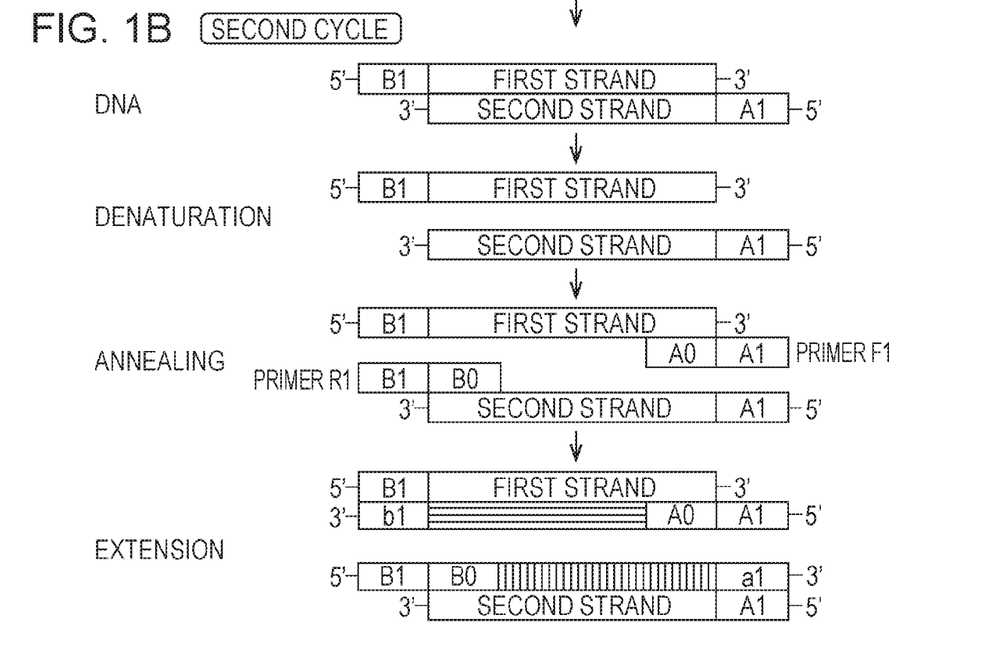
Figure 1C:
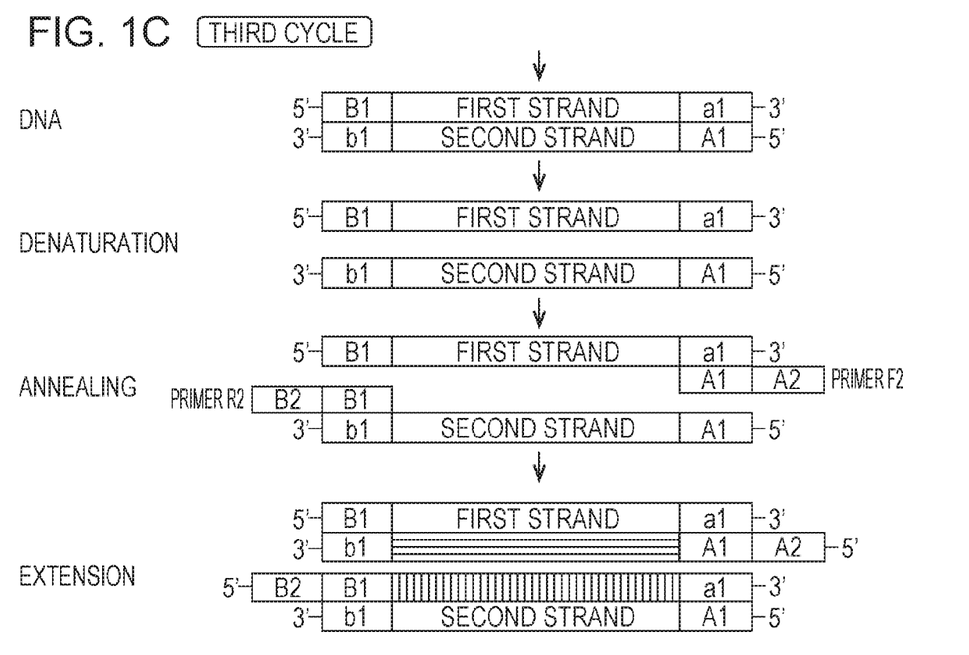
Figure 1D:
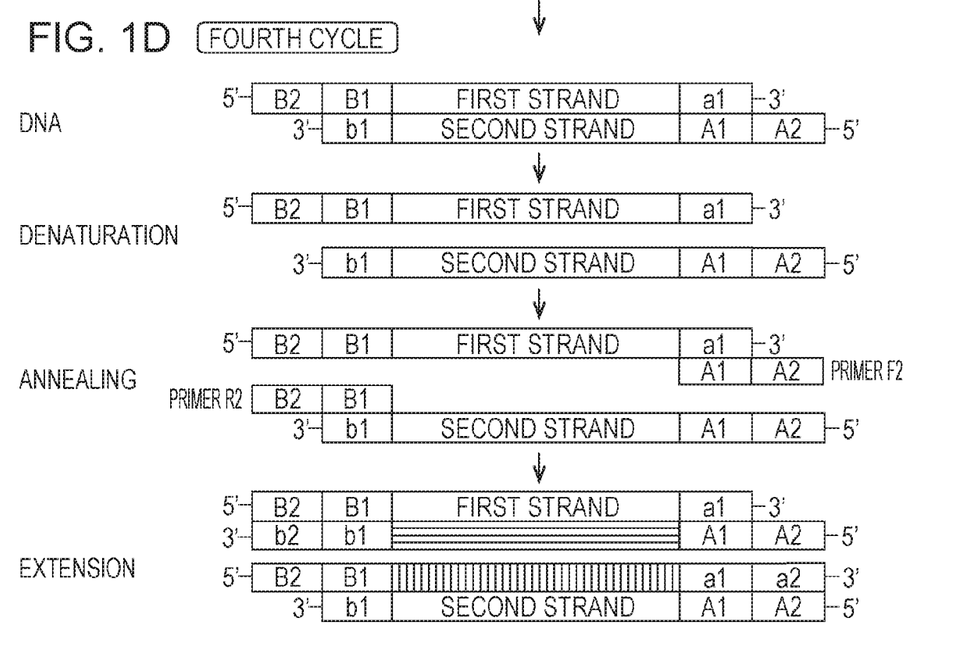
Figure 2A:
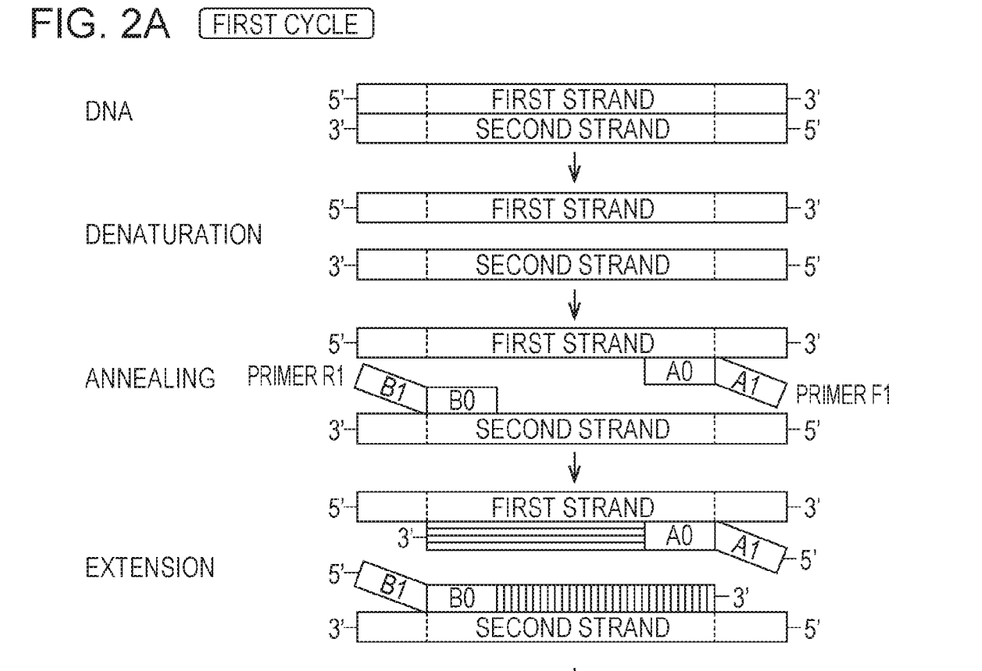
FIGS. 2A to 2D schematically illustrate a DNA amplification method in which both paired primers are primers according to the present invention, and a different primer set is used in each PCR reaction cycle.
Figure 2B:
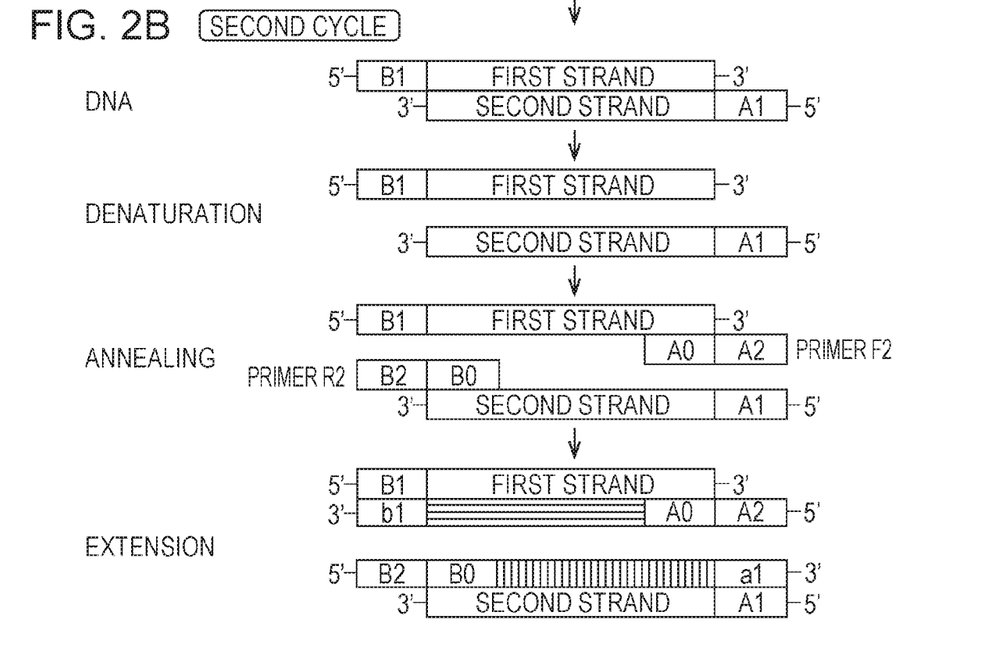
Figure 2C:
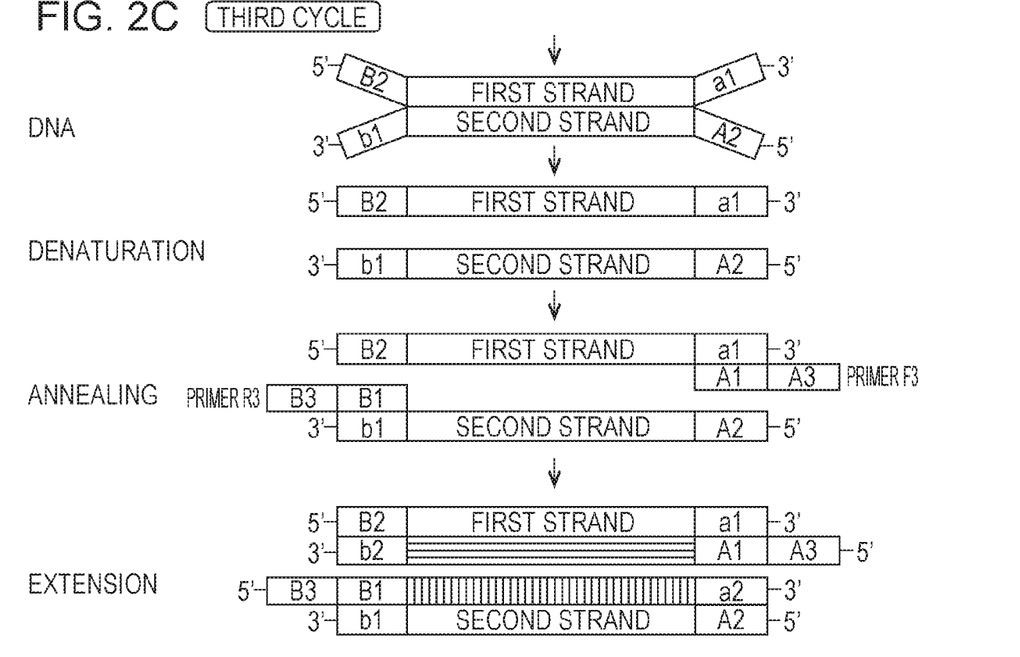
Figure 2D:
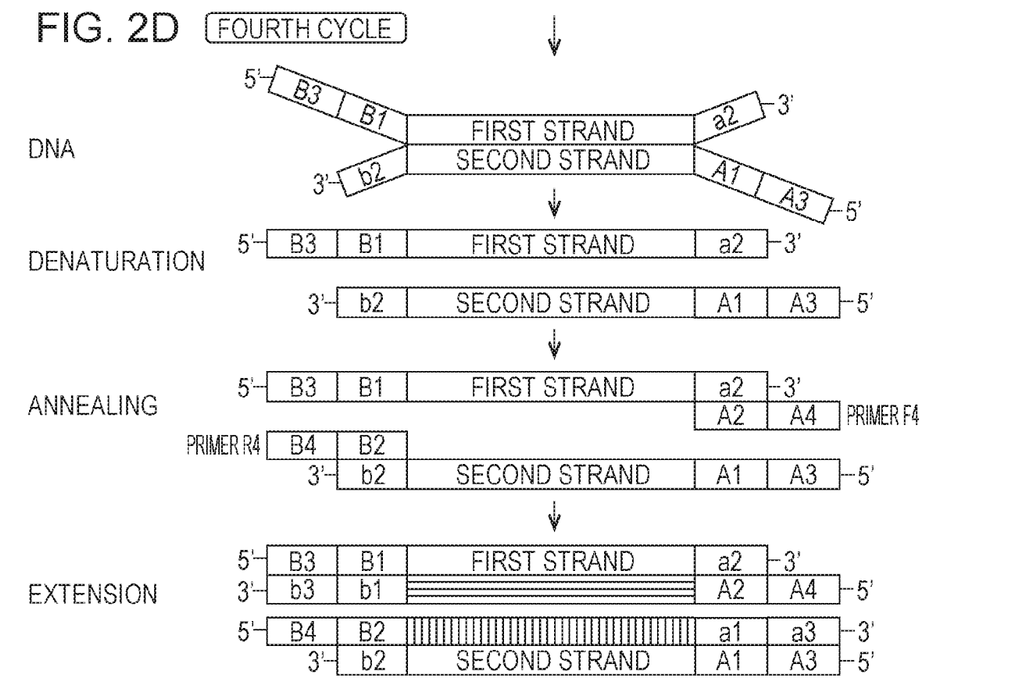
Figure 3A:
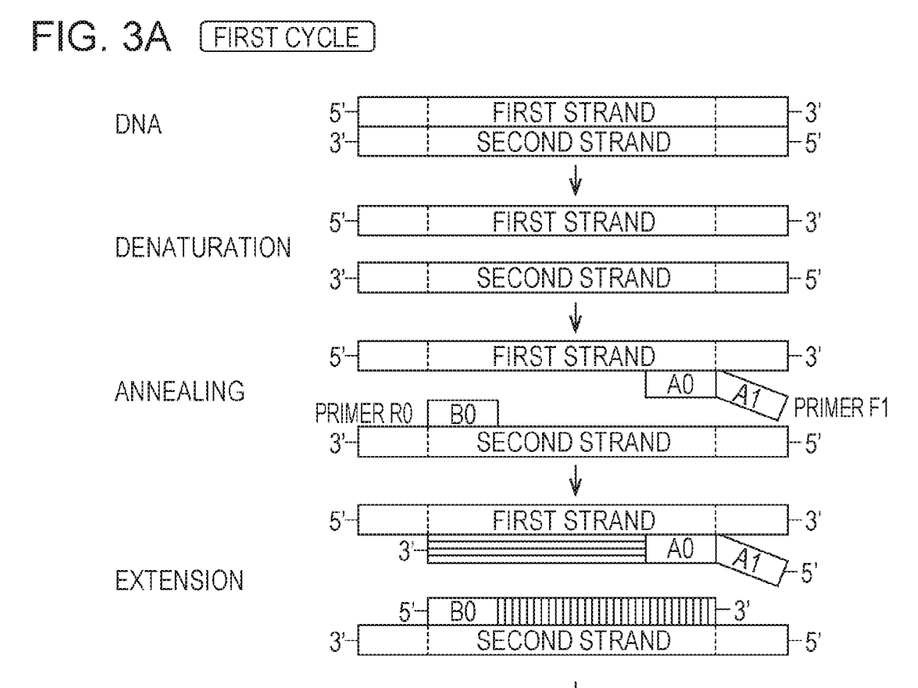
FIGS. 3A to 3D schematically illustrate a DNA amplification method in which only one of paired primers is a primer according to the present invention, and a different primer set is used in each PCR reaction cycle.
Figure 3B:
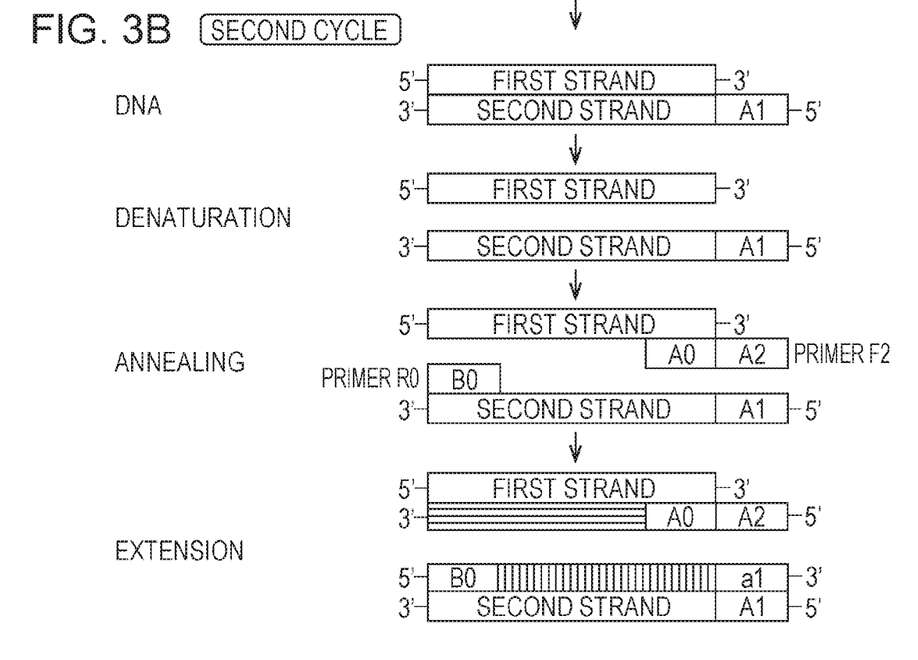
Figure 3C:
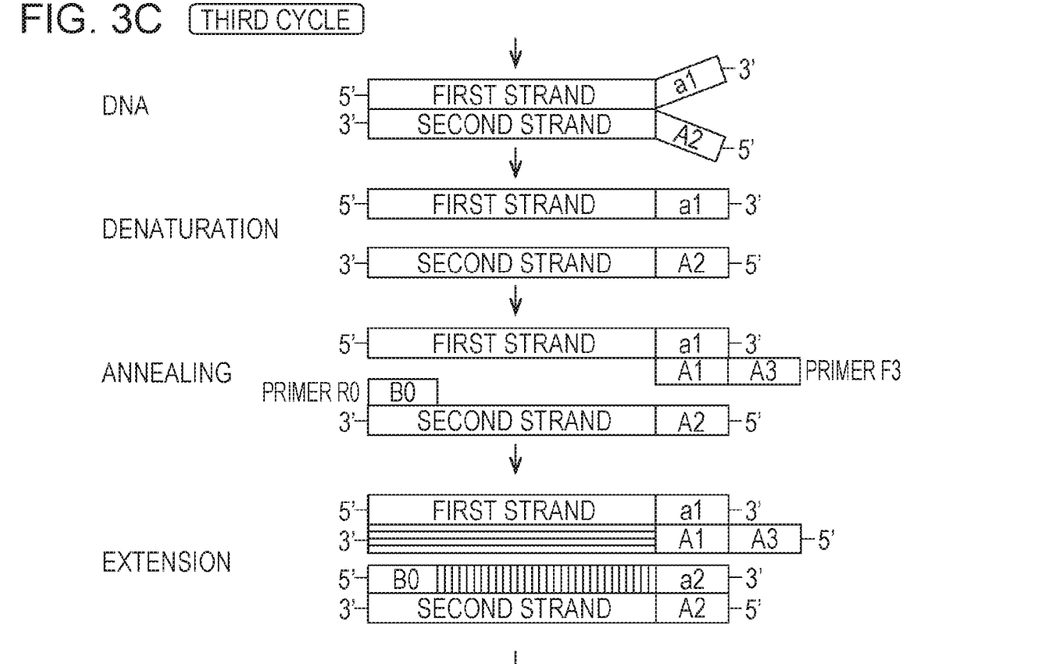
Figure 3D:
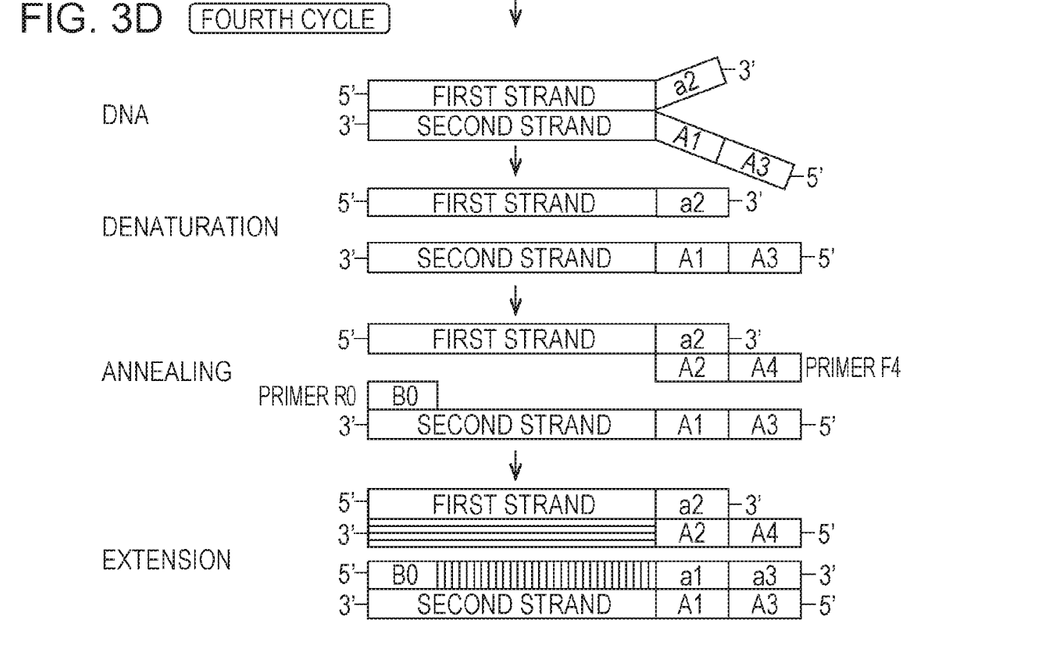

The third cycle of the PCR reaction (refer to FIG. 3C) synthesizes a DNA molecule having, at the 5' end, the base sequence $A_3$ derived from the non-complementary DNA fragment of the primer $F_3$; and a DNA molecule having, at the 3' end, a base sequence $a_2$ (denoted by "a2" in FIG. 3C)

complementary to the base sequence $A_2$ of the non-complementary DNA fragment of the primer $F_2$ used in the second cycle.

In the fourth cycle of the PCR reaction (refer to FIG. 3D), the amplification product generated in the third cycle of the PCR reaction is used as the amplification target DNA (template DNA), a primer set is applied to this amplification target DNA, the primer set being constituted by a primer $F_4$ (denoted by "PRIMER F4" in FIG. 3D) constituted by a complementary DNA sequence constituted by a base sequence $A_2$ annealed with the 3' end side of the amplification target region of the first strand of the amplification target DNA, and a non-complementary DNA fragment constituted by a base sequence $A_4$ (denoted by "A4" in FIG. 3D) that is coupled to the 5' end of the complementary DNA fragment, and that is not annealed with the amplification target region; and a primer $R_0$ constituted by a complementary DNA sequence constituted by a base sequence $B_0$ annealed with the 3' end side of the amplification target region of the second strand of the amplification target DNA.

The fourth cycle of the PCR reaction (refer to FIG. 3D) synthesizes a DNA molecule having, at the 5' end, the base sequence $A_4$ derived from the non-complementary DNA fragment of the primer $F_4$, and a DNA molecule having, at the 3' end, a base sequence $a_3$ (denoted by "a3" in FIG. 3D) complementary to the base sequence $A_3$ of the non-complementary DNA fragment of the primer $F_3$.

In the fifth and subsequent cycles of the PCR reaction, a k+4-th cycle where k represents an integer of 1 or more is also performed with a primer set constituted by primers $F_{k+4}$ and $R_0$.

The primer $F_{k+4}$ is constituted by a complementary DNA fragment constituted by a base sequence $A_{k+2}$, and a non-complementary DNA fragment constituted by a base sequence $A_{k+4}$ that is coupled to the 5' end of the complementary DNA fragment, and that does not complementarily bind to the amplification target region. The base sequence $A_{k+2}$ of the complementary DNA fragment of the primer $F_{k+4}$ is the same as the base sequence $A_{k+2}$ of the non-complementary DNA fragment of the primer $F_{k+2}$. The base sequence $A_{k+4}$ of the non-complementary DNA fragment of the primer $F_{k+4}$ is different from each one of the base sequences $A_1$ to $A_{k+3}$ of the non-complementary DNA fragments of the primer $F_1$ to the primer $F_{k+3}$, and is the same as the base sequence $A_{k+4}$ of the complementary DNA fragment of the primer $F_{k+6}$. As described above, the primer $R_0$ is constituted by the base sequence $B_0$ annealed with the 3' end side of the amplification target region of the second strand of the amplification target DNA.

The k+4-th cycle of the PCR reaction synthesizes a DNA molecule having, at the 5' end, the base sequence $A_{k+4}$ derived from the non-complementary DNA fragment of the primer $F_{k+4}$; and a DNA molecule having, at the 3' end, a base sequence $a_{j+3}$ complementary to the base sequence $A_{j+3}$ of the non-complementary DNA fragment of the primer $F_{j+3}$.

As described above, DNA molecules synthesized in the cycles of the PCR reaction each have, at the 5' end or 3' end, a base sequence enabling identification of the synthesis cycle of the DNA molecule.

This enables identification of, among the thermal cycles of the PCR reaction, the synthesis cycle of a DNA molecule in the amplification product obtained by the PCR reaction, the identification being based on base-sequence data obtained by sequencing the amplification product.

Thus, the synthesis cycles of the synthesized DNA molecules are individually identified, so that the maximum number of PCR times of the amplification target region can also be determined.

Analysis Method

An analysis method according to an embodiment of the present invention is a method for analyzing base-sequence data of an amplification product obtained by amplifying a plurality of regions by supplying a primer set according to the present invention to a PCR reaction, the method including performing correction for each of coverages of the regions in accordance with the number of successful PCR times in the amplification product.

When a plurality of regions are amplified by multiplex PCR, and sequencing is performed with a next-generation sequencer, the regions may exhibit different coverages (the number of reads in the sequencing).

In the analysis method, in the PCR reaction, the synthesis cycles of DNA molecules in amplification products corresponding to regions are identified, the numbers of successful PCR times (maximum numbers of PCR times) for the regions are determined, and correction between the coverages of the regions is performed in accordance with the numbers.

Correction between the coverages of the regions is performed to ensure uniform PCR amplification efficiency between the regions to thereby, for example, enhance the accuracy of determination of chromosome amount.

An analysis method according to another embodiment of the present invention is a method for analyzing base-sequence data of an amplification product obtained by supplying a primer set to a PCR reaction to amplify a region including at least one locus, the method including performing correction for each of coverages of alleles in accordance with the number of successful PCR times in the amplification product.

When polymorphism sites of SNP (single nucleotide polymorphism), CNV (copy number variation), or the like are amplified by PCR, and sequencing is performed with a next-generation sequencer, alleles may exhibit different coverages (the number of reads in the sequencing).

In the analysis method, in the PCR reaction, the synthesis cycles of DNA molecules in amplification products corresponding to alleles are identified, the numbers of successful PCR times (maximum numbers of PCR times) for the alleles are determined, and correction between the coverages of the alleles is performed in accordance with the numbers.

Correction between the coverages of alleles is performed to ensure uniform PCR amplification efficiency between the alleles to thereby, for example, enhance the accuracy of identification of genotype of genetic polymorphism sites.

EXAMPLES

The present invention will be described more specifically with reference to Examples; however, the present invention is not limited to these Examples.

Example 1

A region A and a region B in the human genome are individually present on different chromosomes.

A set of primers for amplifying the region A and the region B is designed in accordance with a method for designing a primer according to the present invention; the primers are synthesized; and multiplex PCR is performed to obtain an amplification product of the region A and the region B.

The amplification product is sequenced with a next-generation sequencer to measure each of a coverage Ca of the region A, a coverage Cb of the region B, a maximum number Ma of PCR times of the region A, and a maximum number Mb of PCR times of the region B.

In order to ensure uniform PCR amplification efficiency between the region A and the region B to enhance the accuracy of determination of chromosome amount, a corrected coverage Cb' of the region B is calculated using the following formula.

$$Cb'=Cb \times 2^{Ma-Mb}$$

Consider a case where the following actual values are obtained: the coverage Ca of the region A=500, the maximum number Ma of successful PCR times=12, the coverage Cb of the region B=100, and the maximum number Mb of PCR times=10. In this case, the corrected coverage Cb' of the region B will be $Cb'=100 \times 2^{(12-10)}=400$. This correction enables accurate estimation of the amounts of chromosomes before PCR.

Example 2

A SNP site A in the human genome has three genotypes: CC, CT, and TT.

A set of primers for amplifying the SNP site A is designed in accordance with a method for designing a primer according to the present invention; the primers are synthesized; and PCR is performed to obtain an amplification product of the SNP site A.

The amplification product is sequenced with a next-generation sequencer to measure each of a read coverage Cc of C at the SNP site A, a read coverage Ct of T at the SNP site A, a maximum number Mc of PCR times for reads of C at the SNP site A, and a maximum number Mt of PCR times for reads of T at the SNP site A.

In order to ensure uniform PCR amplification efficiency between the C allele and the T allele to enhance the accuracy of identification of genotype of the SNP site A, a corrected coverage Ct' of the T allele is calculated using the following formula.

$$Ct'=Ct \times 2^{(Mc-Mt)}$$

Consider a case where the following actual values are obtained: the coverage Cc of the C allele at the SNP site A=500, the coverage Ct of the T allele at the SNP site A=100, the maximum number Mc of PCR times for the C allele at the SNP site A=12, and the maximum number Mt of PCR times for the T allele at the SNP site A=10. In this case, a corrected coverage Ct' of the T allele will be $Ct'=100 \times 2^{(12-10)}=400$.

This correction enables enhancement of the accuracy of identifying genotype of the SNP site A to be CT.

The present invention is applicable to, in gene analysis such as determination of chromosome count or SNP analysis, correction of coverage data or the like to perform accurate analysis.

What is claimed is:

1. A method for designing a primer supplied to a PCR reaction, the method comprising:
a primer designing step of including a base sequence or its complementary base sequence on a 5'-end-side base sequence of the primer, the base sequence enabling identification at which cycle of thermal cycles in the PCR reaction a DNA molecule in an amplification product obtained by the PCR reaction performed with the primer is synthesized, the identification being based on base-sequence data obtained by sequencing the amplification product.

2. The method for designing a primer supplied to a PCR reaction according to claim 1,
wherein, in the primer designing step,
the primer is a primer used in N-th and N+1-th thermal cycles,
N represents an odd number of 1 or more,
when N=1, the step includes coupling a non-complementary DNA fragment to a 5' end of a complementary DNA fragment,
the complementary DNA fragment being constituted by a base sequence that complementarily binds to a 3' end side of an amplification target region in amplification target DNA; the non-complementary DNA fragment being constituted by a base sequence that does not complementarily bind to the amplification target region; and
when N≥3, the step includes coupling a non-complementary DNA fragment to a 5' end of a complementary DNA fragment,
the complementary DNA fragment being constituted by a base sequence of a non-complementary DNA fragment of a primer used in an N−2-th thermal cycle; the non-complementary DNA fragment being constituted by a base sequence that is different from each one of base sequences of non-complementary DNA fragments of primers used in 1st to N−2-th thermal cycles, and that does not complementarily bind to the amplification target region.

3. The method for designing a primer supplied to a PCR reaction according to claim 1,
wherein, in the primer designing step,
the primer is a primer used in an N-th thermal cycle,
N represents an integer of 1 or more,
when N=1, the step includes coupling a non-complementary DNA fragment to a 5' end of a complementary DNA fragment,
the complementary DNA fragment being constituted by a base sequence that complementarily binds to a 3' end side of an amplification target region in amplification target DNA; the non-complementary DNA fragment being constituted by a base sequence that does not complementarily bind to the amplification target region;
when N=2, the step includes coupling a non-complementary DNA fragment to a 5' end of a complementary DNA fragment,
the complementary DNA fragment being constituted by a base sequence that complementarily binds to a 3' end side of an amplification target region in amplification target DNA; the non-complementary DNA fragment being constituted by a base sequence that is different from the base sequence of the non-complementary DNA fragment of the primer used in the 1st thermal cycle, and that does not complementarily bind to the amplification target region; and
when N≥3, the step includes coupling a non-complementary DNA fragment to a 5' end of a complementary DNA fragment,
the complementary DNA fragment being constituted by a base sequence of a non-complementary DNA fragment of a primer used in an N−2-th thermal cycle; the non-complementary DNA fragment being constituted by a base sequence that is different from each one of base sequences of non-complementary DNA fragments of primers used in 1st to N−1-th thermal cycles, and that does not complementarily bind to the amplification target region.

4. A primer designed by the method for designing a primer according to claim 1.

5. A primer set supplied to a PCR reaction, the primer set comprising the primer according to claim 4.

6. A primer set supplied to a PCR reaction, the primer set comprising a plurality of the primer sets according to claim 5.

7. A DNA amplification method comprising supplying the primer set according to claim 5 to a PCR reaction.

8. A method for analyzing base-sequence data of an amplification product obtained by supplying the primer set according to claim 5 to a PCR reaction to amplify a plurality of regions, the method comprising:
  identifying, in the PCR reaction, the synthesis cycles of DNA molecules in amplification products corresponding to regions,
  determining the numbers of successful PCR times for the regions, and
  performing correction between coverages of the regions in accordance with the numbers to ensure uniform PCR amplification efficiency between the regions.

9. A method for analyzing base-sequence data of an amplification product obtained by supplying the primer set according to claim 6 to a PCR reaction to amplify a plurality of regions, the method comprising:
  identifying, in the PCR reaction, the synthesis cycles of DNA molecules in amplification products corresponding to regions,
  determining the numbers of successful PCR times for the regions, and
  performing correction between coverages of the regions in accordance with the numbers to ensure uniform PCR amplification efficiency between the regions.

10. A method for analyzing base-sequence data of an amplification product obtained by supplying the primer set according to claim 5 to a PCR reaction to amplify a region including at least one locus, the method comprising:
  identifying, in the PCR reaction, the synthesis cycles of DNA molecules in amplification products corresponding to alleles,
  determining the numbers of successful PCR times for the alleles, and
  performing correction between coverages of the alleles in accordance with the numbers to ensure uniform PCR amplification efficiency between the alleles.

11. A method for analyzing base-sequence data of an amplification product obtained by supplying the primer set according to claim 6 to a PCR reaction to amplify a region including at least one locus, the method comprising:
  identifying, in the PCR reaction, the synthesis cycles of DNA molecules in amplification products corresponding to alleles,
  determining the numbers of successful PCR times for the alleles, and
  performing correction between coverages of the alleles in accordance with the numbers to ensure uniform PCR amplification efficiency between the alleles.

* * * * *